(12) United States Patent
Sanghera et al.

(10) Patent No.: US 10,105,075 B2
(45) Date of Patent: Oct. 23, 2018

(54) IMPLANTABLE CARDIAC DEVICE SENSING WITH REFRACTORY PERIOD ALIGNMENT TO SIGNAL PEAK

(71) Applicant: Cameron Health, Inc., San Clemente, CA (US)

(72) Inventors: Rick Sanghera, San Clemente, CA (US); Venugopal Allavatam, San Clemente, CA (US); Mark Schroeder, San Clemente, CA (US)

(73) Assignee: Cameron Health, Inc., St. Paul, MN (US)

( * ) Notice: Subject to any disclaimer, the term of this patent is extended or adjusted under 35 U.S.C. 154(b) by 1375 days.

(21) Appl. No.: 13/898,711

(22) Filed: May 21, 2013

(65) Prior Publication Data

US 2014/0350423 A1    Nov. 27, 2014

(51) Int. Cl.
*A61B 5/04* (2006.01)
*A61B 5/0472* (2006.01)
*A61B 5/0456* (2006.01)

(52) U.S. Cl.
CPC .......... *A61B 5/0472* (2013.01); *A61B 5/0456* (2013.01); *A61B 5/04* (2013.01)

(58) Field of Classification Search
USPC ....................................................... 600/521
See application file for complete search history.

(56) References Cited

U.S. PATENT DOCUMENTS

| | | | |
|---|---|---|---|
| 5,709,215 A | 1/1998 | Perttu et al. | |
| 6,505,068 B2 | 1/2003 | Bonnet et al. | |
| 6,647,292 B1 | 11/2003 | Bardy et al. | |
| 6,721,597 B1 | 4/2004 | Bardy et al. | |
| 6,754,528 B2 | 6/2004 | Bardy et al. | |
| 7,149,575 B2 | 12/2006 | Ostroff et al. | |
| 7,194,302 B2 | 3/2007 | Bardy et al. | |
| 7,330,757 B2 | 2/2008 | Ostroff et al. | |
| 8,160,686 B2 | 4/2012 | Allavatam et al. | |
| 8,160,687 B2 | 4/2012 | Warren et al. | |
| 8,265,737 B2 | 9/2012 | Warren et al. | |
| 2009/0228057 A1 | 9/2009 | Allavatam et al. | |
| 2010/0331904 A1 | 12/2010 | Warren et al. | |
| 2011/0098585 A1* | 4/2011 | Warren | A61B 5/0452 600/509 |
| 2011/0098775 A1 | 4/2011 | Allavatam et al. | |
| 2012/0046563 A1 | 2/2012 | Allavatam et al. | |
| 2012/0271185 A1* | 10/2012 | Sanghera | A61N 1/36592 600/516 |

* cited by examiner

*Primary Examiner* — Christopher D Koharski
*Assistant Examiner* — Elizabeth K So
(74) *Attorney, Agent, or Firm* — Seager, Tufte & Wickhem LLP

(57) ABSTRACT

Methods and devices for addressing difficulty with cardiac event sensing that can arise if the starting point of the cardiac cycle is not well aligned to the intended starting point of a detection profile used for sensing. As an improvement, illustrative methods and devices provide an addition to cardiac sensing operations by adjusting the starting point of a detection profile to align with a desired point in the cardiac signal.

20 Claims, 9 Drawing Sheets

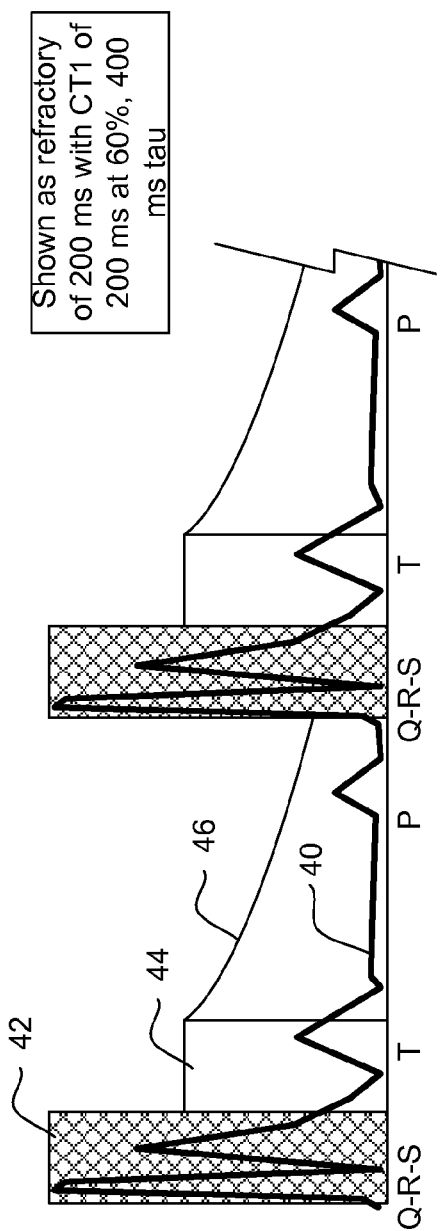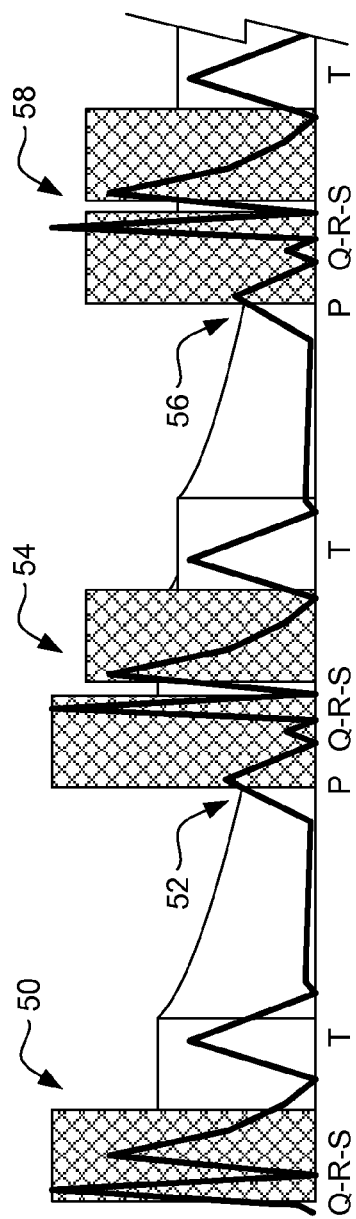

IMPLANTABLE CARDIAC DEVICE SENSING WITH REFRACTORY PERIOD ALIGNMENT TO SIGNAL PEAK

BACKGROUND

Implantable cardiac rhythm management devices are widely used in medicine. Some illustrative devices include implantable cardiac monitors, such as an implantable loop recorder, implantable pacemakers, implantable defibrillators, and implantable cardiac resynchronization systems.

Some implantable cardiac rhythm management devices are configured to sense cardiac activity of a patient and detect individual cardiac cycles or "beats" of the patient. To perform such sensing, systems sometimes make use of a detection profile. Some examples of detection profiles are shown in U.S. Pat. No. 5,709,215 to Perttu et al. and U.S. Published Patent Application No. 2009-0228057, titled ACCURATE CARDIAC EVENT DETECTION IN AN IMPLANTABLE CARDIAC STIMULUS DEVICE, the disclosures of which are incorporated herein by reference.

There are numerous ways that such systems and sensing methods can encounter difficulties. Underdetection or dropout, where a cardiac cycle goes uncounted, and overdetection, where a cardiac cycle is counted more than once, are two examples. Misdetection, where a cardiac cycle is counted but not in the manner planned, is another example. Noise detection, where a signal that is non-cardiac is counted, is yet another example. All of these are types of malsensing. Alternatives and new enhancements that reduce malsensing are desired.

Overview

The Inventors have recognized that difficulty with cardiac event sensing can arise if the starting point of the cardiac cycle is not well aligned to the intended starting point of a detection profile used for sensing. As an improvement, the Inventors have identified an addition to the cardiac sensing method that, in an illustrative example, includes adjusting the starting point of the detection profile to align with a desired point in the cardiac signal.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 2 shows application of an illustrative detection profile to a cardiac signal;

FIG. 3 shows an example of overdetection of the cardiac signal using a detection profile;

Figure 1:
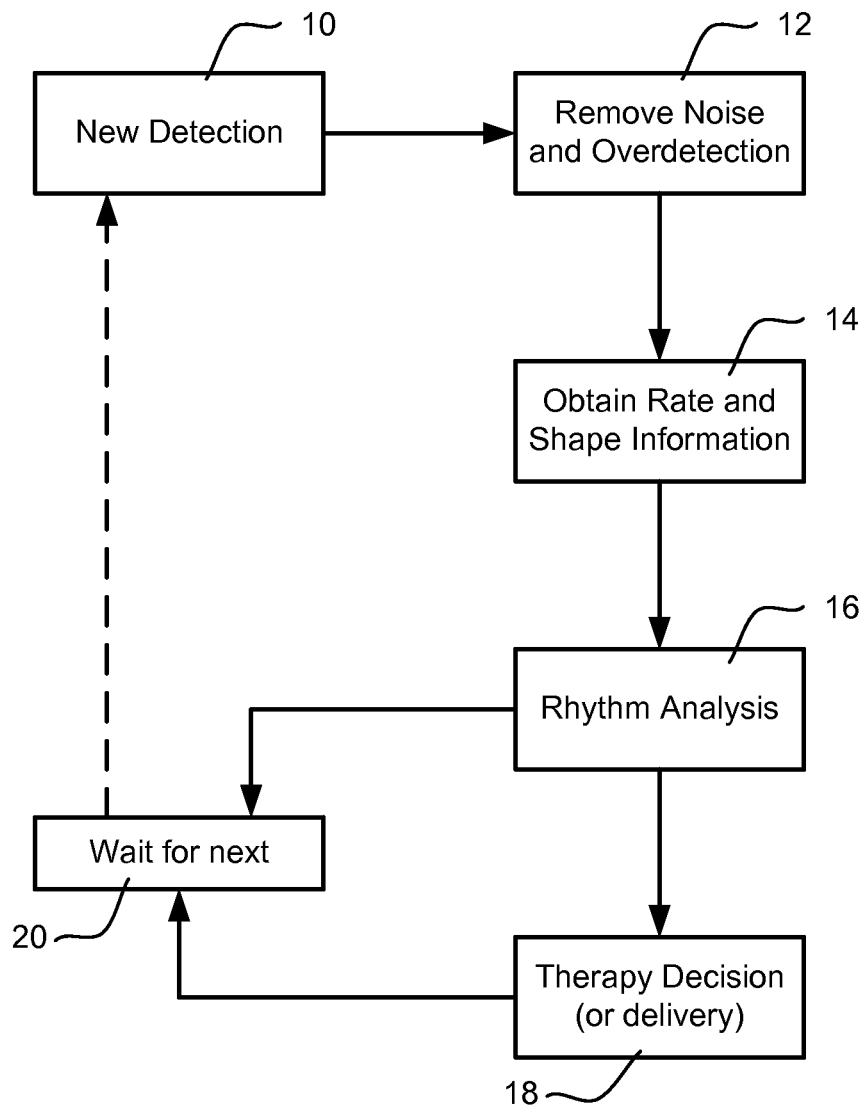
FIG. 1 shows, in block form, a method of cardiac signal analysis for an implantable medical device.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Each of the following non-limiting examples can stand on its own, or can be combined in various permutations or combinations with one or more of the other examples.

As used herein, a signal is sensed by an implantable cardiac device system, events are detected in the sensed signal, and cardiac rhythms are classified by use of the detected events. Detected events may also be referred to as detections. Classification of the cardiac rhythms may be referred to as rhythm analysis. Cardiac rhythm classification can include identification of malignant conditions, such as ventricular fibrillation or certain tachyarrhythmias, for example.

The present invention may be used in implantable monitoring or therapy systems. Implantable therapy systems make therapy/stimulus decisions in reliance upon rhythm classification, while monitoring systems make data recording decisions using rhythm classification, where applicable. Therapy systems may deliver electrical, pharmaceutical or other therapy. Some illustrative implementations of the present invention may be in pacemakers and defibrillators, though other implementations are also envisioned. Any of these systems can, if so configured and enabled, generate annunciating (audible tones or palpable vibrations) or communicating (telemetry) signals in response to rhythm classification, in addition to or as an alternative to therapy.

FIG. 1 shows, in block form, a method of cardiac signal analysis for an implantable medical device. The analysis is cyclic and can be understood as beginning with a new detection or detected event 10. Illustrative detection methods are shown below and may be understood as well from US Published Patent Application No. 2009-0228057, titled ACCURATE CARDIAC EVENT DETECTION IN AN IMPLANTABLE CARDIAC STIMULUS DEVICE, the disclosure of which is incorporated herein by reference. Other detection methods may be used instead.

Once a detected event is identified, the analysis then performs assessments to identify noise and/or overdetection as shown at 12. Noise may be identified, for example, as shown in US Published Patent Application No. 2011-0098775, titled ADAPTIVE WAVEFORM APPRAISAL IN AN IMPLANTABLE CARDIAC SYSTEM, the disclosure of which is incorporated herein by reference. Overdetection may be identified, for example, as shown in U.S. Pat. Nos. 8,160,686 and 8,160,687, each titled METHODS AND DEVICES FOR ACCURATELY CLASSIFYING CARDIAC ACTIVITY, U.S. Pat. No. 8,265,737, titled METHODS AND DEVICES FOR IDENTIFYING OVERDETECTION OF CARDIAC SIGNALS, and/or US Published Patent Application No. 2012-0046563, titled METHODS AND DEVICES THAT IDENTIFY OVERDETECTION IN IMPLANTABLE CARDIAC SYSTEMS, the disclosures of which are incorporated herein by reference. Other noise identification and/or overdetection identification methods may be used instead to address malsensing and enhance the accuracy of counting of cardiac cycles.

Next, the analysis method obtains certain useful data such as rate and shape information, as shown at 14. Rate and shape information may then be used for rhythm analysis 16. If the rhythm analysis at 16 determines that therapy may be needed, a therapy decision can be made, as shown at 18. The analysis then waits for the next new detection, as shown at 20.

Illustrative methods useful in blocks 14, 16 and/or 18 are shown in the above incorporated patents and published patent applications as well as U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR, U.S. Pat. No. 7,330,757, titled METHOD FOR DISCRIMINATING BETWEEN VENTRICULAR AND SUPRAVENTRICULAR ARRHYTHMIAS, US Published Patent Application No. 2010-0331904, titled ADAPTIVE CONFIRMATION OF TREATABLE ARRHYTHMIA IN IMPLANTABLE CARDIAC STIMULUS DEVICES, and US Published Patent Application No. 2012-0271185, titled ROBUST RATE CALCULATION IN AN IMPLANTABLE CARDIAC STIMULUS OR MONITORING DEVICE, the disclosures of which are each incorporated herein by reference. In addition to these patents and patent applications, various methods are known in the art from various commercially available implementations.

As noted above in the Background, there are several different types of malsensing that can occur, including overdetection, underdetection, misdetection, and noise detection. As shown by FIG. 1, there are various mitigations for malsensing that may include noise identification and overdetection identification. These enhancements can assist the system in generating an accurate count of cardiac events, which can be used to estimate rate.

FIG. 2 shows application of an illustrative detection profile to a cardiac signal. A cardiac cycle typically includes several portions (often referenced as "waves") which, according to well-known convention, are labeled with letters including P, Q, R, S, and T, each corresponding to certain physiological events. A normal cardiac cycle usually has all of these parts, though not all may be visible on any given cardiac signal representation. Certain components may not be visible due to factors such as elevated rate, choice of sensing vector, anatomic anomaly, or active arrhythmia, for example. The combination of Q, R and S "waves" can be referred to as the QRS complex. The R-wave and/or QRS complex is often the component of the cardiac cycle that is detected for purposes of identifying a cardiac cycle, since it is typically the largest amplitude component. In some examples, other components may be the target for detection instead, such as the atrial depolarization or P-wave.

In FIG. 2, a cardiac signal is shown at 40, with indications of the Q, R, S, T and P waves shown below the line. An illustrative detection profile is shown including a refractory period 42, a constant threshold period 44 and a decay period 46. The refractory period defines a time during which the system's operational circuitry will not detect an event, while the constant threshold period and decay period collectively define a time period during which the system's operational circuitry will detect an event if the sensed signal 40 crosses one of lines 44 or 46.

The detection profile 42/44/46 relies in part on the "estimated peak" of the QRS complex. The estimated peak is a measure of amplitude or magnitude, depending on the particulars of a given embodiment, of the cardiac signal being monitored. As the signal grows larger, so too does the estimated peak. In some examples, an estimated peak is the largest peak in a given QRS complex. In other examples, the estimated peak is an average of the largest peaks in the previous two detected cardiac events. Other measures, averages or the like may be used. Estimated peak may be used, for example, by setting the amplitude for the constant threshold period 44 at a percentage of the estimated peak, and/or by setting the beginning point of the decay period 46 to a fraction of the estimated peak.

As shown in FIG. 2, accurate detection of the QRS complex occurs, as the refractory period 42 lasts long enough to cover the entire QRS complex, and the combined constant threshold period 44 and decay period 46 pass over the T-wave and P-wave without an additional detection occurring. That the detection is accurate is observed by noting that there is one refractory period 42, shown in the cross hatching, for each QRS complex.

In the illustrative example shown, as noted in the drawing, a refractory period of 200 milliseconds is applied, with the constant threshold period 44 set to an amplitude that is 60% of the R-wave peak amplitude for a duration of 200 milliseconds. The decay period 46 uses a time constant, tau, of 400 milliseconds. These durations, percentages and time constants may all change in other embodiments and those shown are merely illustrative.

FIG. 3 shows an example of overdetection of the cardiac signal using a detection profile. Here, it can be seen that there is only one refractory period (shown again in cross hatching) for the leftmost QRS complex 50, but there are two refractory periods for the subsequent QRS complexes shown at 54 and 58. In particular, as shown at 52, the P-wave for the QRS complex 54 crosses the detection profile threshold well in advance of the QRS complex 54. As a result, the refractory period ends before the QRS complex 54 finishes, leading to a second detection of the same QRS complex.

In the illustrative example, the overdetection also causes a reduction of the estimated peak. As shown at 54, the R-wave is captured under the first refractory period, but not under the second refractory period. As a result, the system will perceive the peak amplitude to be lower for the overdetected event. This can increase the likelihood of additional overdetections since the peak amplitudes can be used to define the sensitivity. A lower peak amplitude can increase sensitivity and add to the overdetection by lowering the estimated peak.

One response to overdetection is to perform analysis designed to identify and remove detected events caused by overdetection. Such analysis can be computationally intensive and, if unsuccessful, increases the chances of the patient receiving inappropriate therapy. Further, additional tools to avoid overdetection in the first place can reduce the risk of overdetection going unnoticed and leading to inappropriate therapy.

Figure 4:
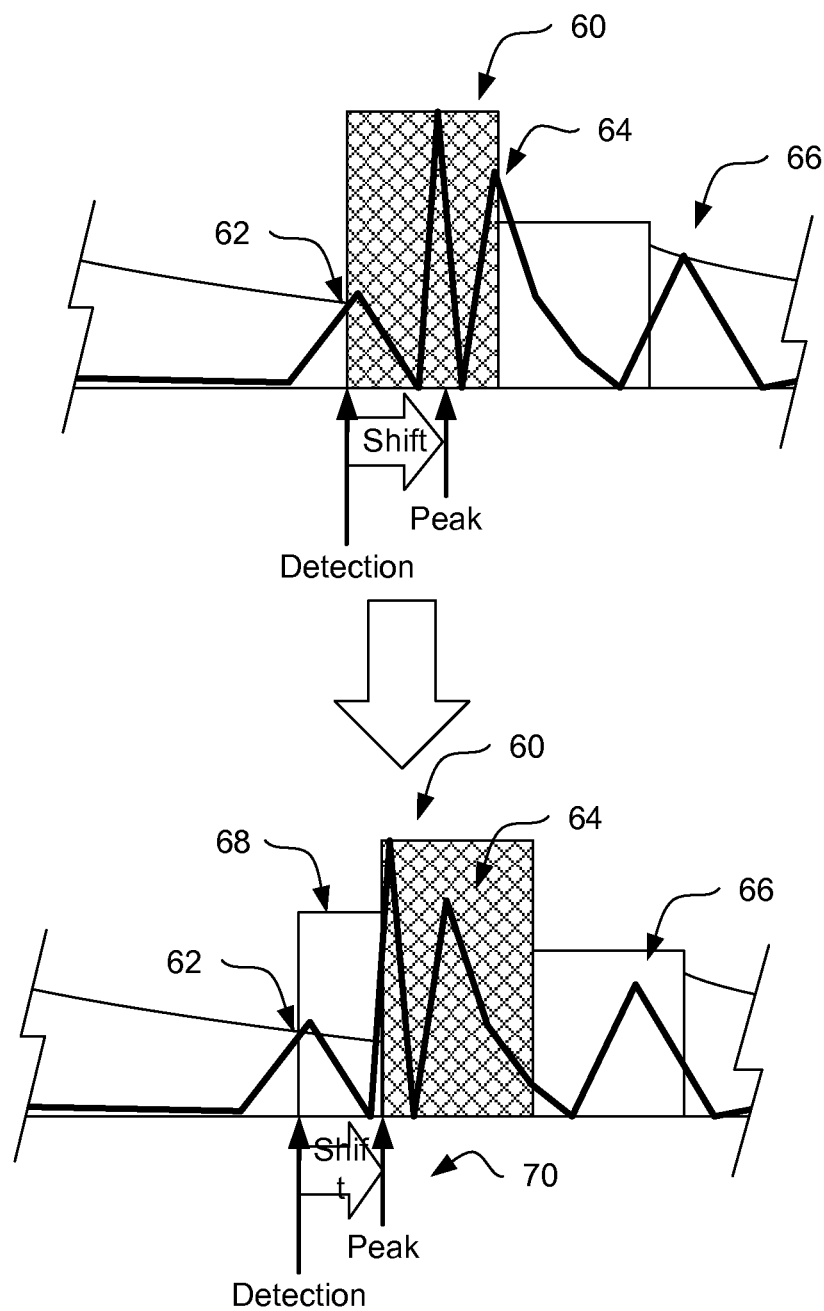
FIG. 4 illustrates a shifting alignment of the refractory period of a detection profile relative to a cardiac event peak.

FIG. 4 illustrates a shifting alignment of the refractory period of a detection profile relative to a cardiac event peak. The illustrative example is based on detection of a P-wave for illustrative purposes. Other root causes for overdetection may also be addressed.

As shown in the upper drawing, the QRS complex at 60 has been detected upon crossing of the detection profile by the P-wave, as shown at 62. In the prior art, the refractory period would typically start at the point of the detection, 62, as shown in the upper drawing. This can lead to overdetection of the trailing part of the QRS complex 64 and/or the T-wave as highlighted at 66.

The solution, as shown in FIG. 4, is to shift the start of the refractory period toward the peak that occurs during the refractory period. By shifting the refractory period by an interval 68 to the peak 70, rather than the detection itself 62, the refractory period is aligned with the main portion of the QRS complex. As a result, the trailing edge of the QRS complex 64 occurs during refractory, and the T-wave 66 occurs during and below the constant threshold and is therefore not detected. As illustrated by FIG. 4, the likelihood of overdetection may be reduced by shifting the refractory period start closer to the desired peak.

Figure 5:
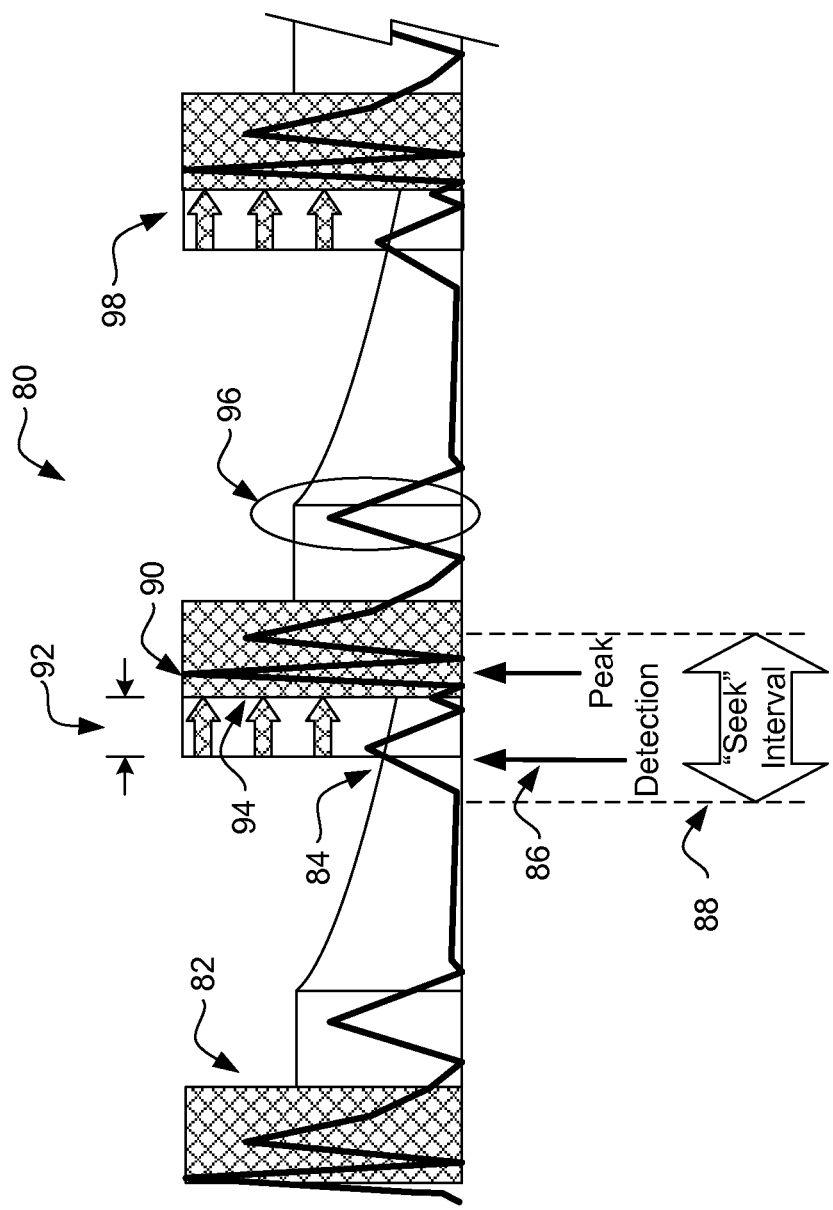
FIG. 5 illustrates the application of refractory alignment relative to the cardiac signal peak.

FIG. 5 illustrates the application of refractory alignment relative to the cardiac signal peak and provides several illustrative ways of applying such a shift. A cardiac signal and detection profile treatment of the signal is shown at 80. In the example, a detected event occurs at 82 causing the application of an illustrative detection profile. At 84, the threshold defined by the detection profile is crossed, in this case by a P-wave, resulting in a detection 86.

Upon receipt of the detection, in the illustrative method, the system seeks the highest amplitude point during a "Seek" Interval, as shown at 88. In the example shown, the highest amplitude point is at peak 90. Therefore the refractory period starting point will be shifted in the direction of the peak 90. The highest amplitude point is sought in the "Seek" Interval 88 and that point may not necessarily be a peak in the signal if the peak is not in the "Seek" Interval 88. Alternatively, the greatest magnitude point may be sought, depending upon how the signal processing takes place.

In this example, an additional rule is applied which restricts the extent of refractory period shifting to a limit illustrated at 92. Thus the refractory period start is not shifted all the way to the peak 90, but only as far as limit 92 allows. The shift is shown at 94.

As a result of the shift 94, the T-wave at 96 is not detected by the detection profile. Without the shift 94, the T-wave could have been detected, potentially starting an overdetection pattern. This process of shifting the refractory start is repeated at 98.

Several variants can be used:
  The refractory period start may be shifted in the direction of the highest amplitude point during a "Seek" Interval defined relative to the detection point. The interval may include just the time following the detection point, or it may include time before the detection occurs, as shown by FIG. 5.
  The extent of shifting of the refractory period start may be limited by the length of the "Seek" Interval itself, or it may be limited, as shown in FIG. 5, by a different value.
  A separate rule may be stated for the amount of shift, such as shifting so that the start of refractory occurs at an inflection point adjacent to the highest point found during the "Seek" Interval
  The shift of the start of refractory may be to a point that is some predefined interval (such as 10-60 milliseconds or some other duration) away from the highest point found in the "Seek" Interval, or a peak nearest the highest point found in the "Seek" Interval
  Rather than a particular peak in the signal, shifting may be based on the location of a maximum slope point or first or second derivative zero, or other signal information element
  In one example, a fiducial point may be defined for a template used in correlation comparisons to the cardiac signal. The template may be compared to the signal by time-shifting the signal relative to the fiducial point until a peak correlation is identified. The "shifting" of the start of refractory may be performed to match or accommodate the time shifting that is performed for correlation purposes.
  In another example, rather than thinking of a shift of the start of the refractory period, the refractory period can always begin at the point of detection, but the end of the refractory period is shifted to a particular distance following the identified peak or other "shifting" point in the sensed signal. This approach would call for longer and shorter refractory periods depending upon the sensed signal.

Figure 6A:
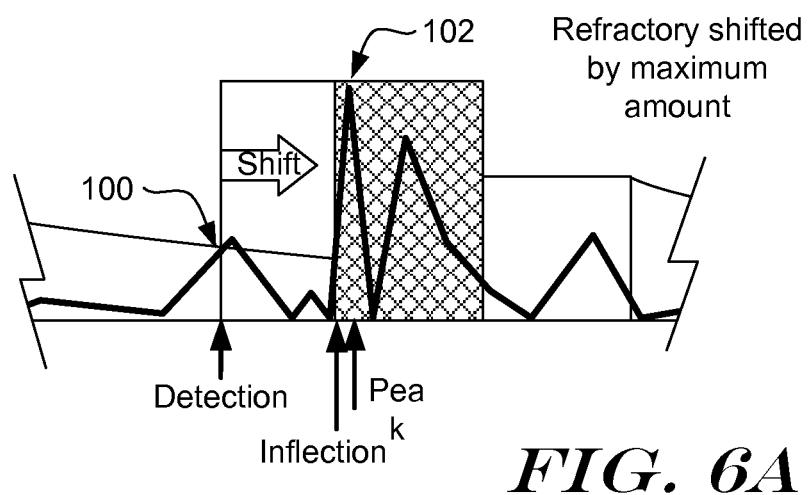
FIGS. 6A-6B show application of different rules for refractory alignment relative to cardiac signal peaks.
Figure 6B:
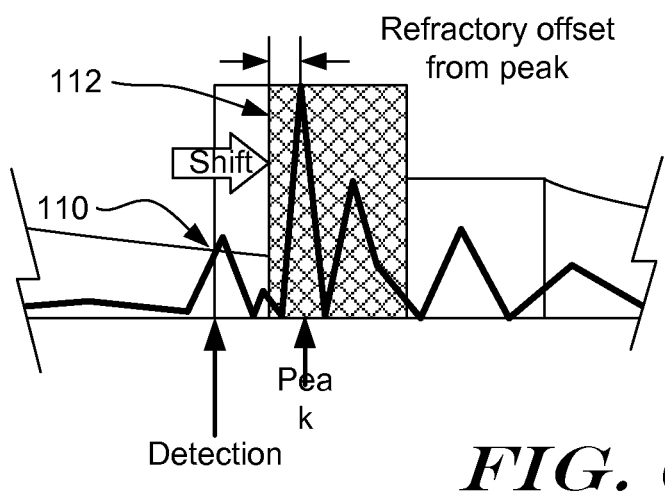

FIGS. 6A-6B show application of different rules for refractory alignment relative to cardiac signal peaks. In FIG. 6A, a detection occurs at 100. A peak is identified at 102, and the inflection point just before the peak 102 is also identified. The refractory period start is shifted to the identified inflection point.

In FIG. 6B, a detection occurs at 110. The peak is identified, and the shift of the refractory period start is performed, as shown at 112, so that the refractory period starts 50 ms before the R-wave peak.

Figure 7A:
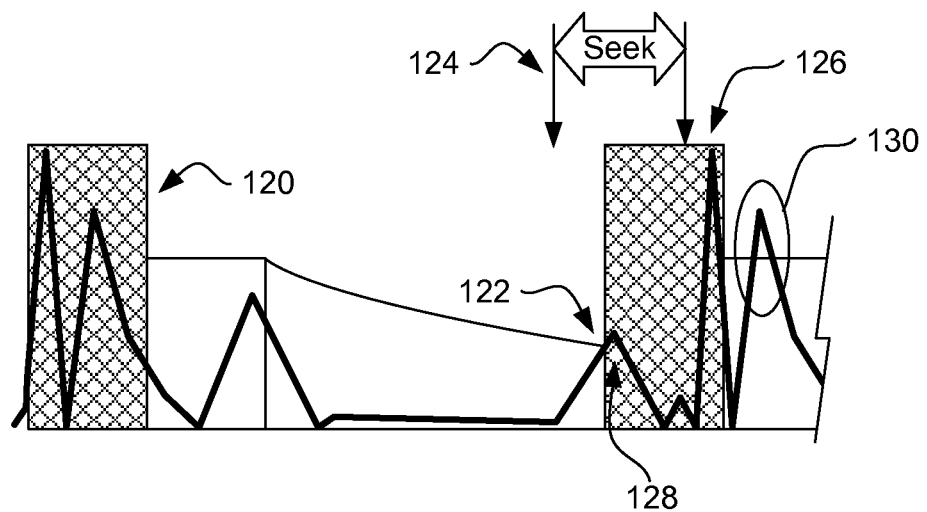
FIGS. 7A-7B illustrate peak seeking before and after a detection occurs and realignment of the refractory start relative to an identified peak.
Figure 7B:
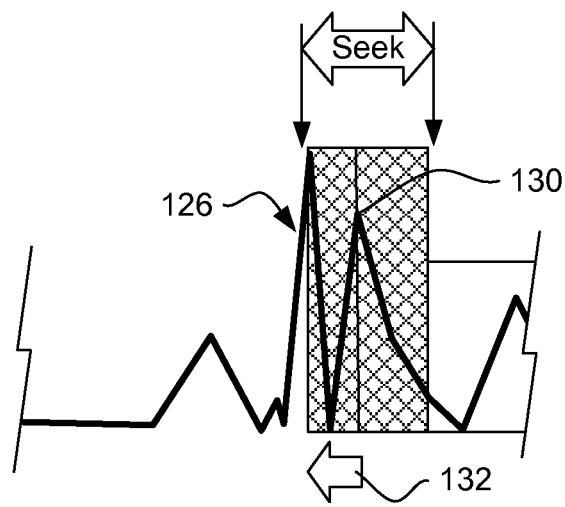

FIGS. 7A-7D illustrate peak searching before and after a detection occurs and realignment of the refractory start relative to an identified peak. In this example, following a detection at 120, the P-wave leads to an early detection as shown at 122. The seek interval, shown at 124, does not capture the R-wave 126 or R-wave start, so that the refractory period is set to start as shown at 128 at the same time as the P-wave peak. This causes an overdetection of the trailing part of the QRS complex at 130. FIG. 7B, when viewed in combination with FIG. 7A, illustrates one way of ensuring regular overdetection.

In FIG. 7B, the overdetection of the trailing part of the QRS complex is subject to the same Seek period, which now captures the R-wave 126. As a result, the start of the refractory period will be shifted 132 backward to the R-wave peak, from peak 130 back to peak 126. In this instance, the shifting may not prevent overdetection from taking place, but it will normalize the overdetection to assist in subsequent correction. For example, if an overdetection identification algorithm relies on pattern identification, normalizing the detection may improve the pattern recognition.

In some examples, an automatic double detection flag can be set whenever the start of the refractory period is shifted backward in time as shown by FIG. 7B. In other examples, if the shifting backward in time would cause two refractory periods to overlap, an automatic double detection flag can be set. Once a double detection flag is set, in some examples, detection data can be corrected to combine the double detected events into one event. In other examples, an identified double detection may be relied upon to inhibit therapy deliver that would otherwise take place, with or without correcting detection data.

Figure 7C:
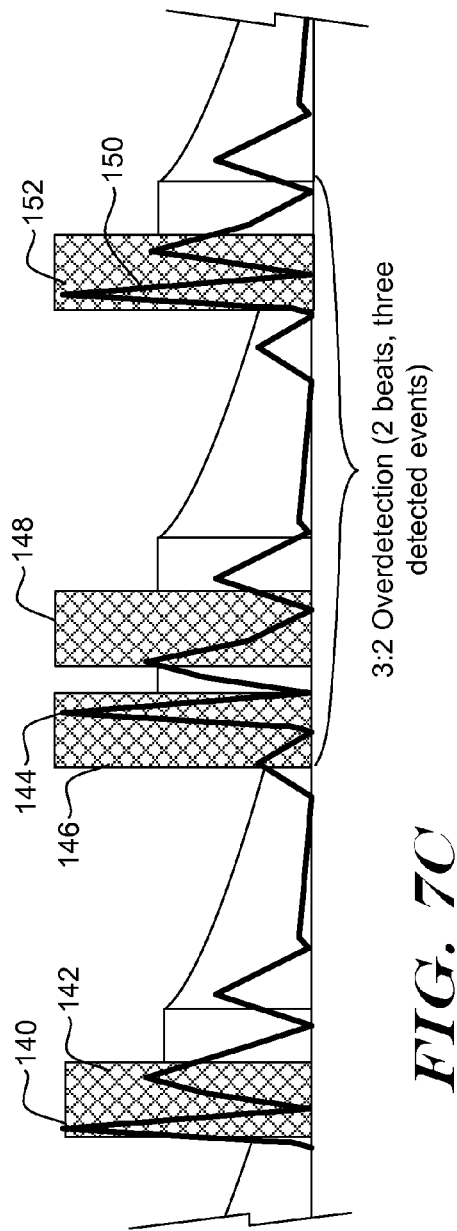
FIGS. 7C-7D illustrate conversion of inconsistent overdetection to consistent overdetection.
Figure 7D:
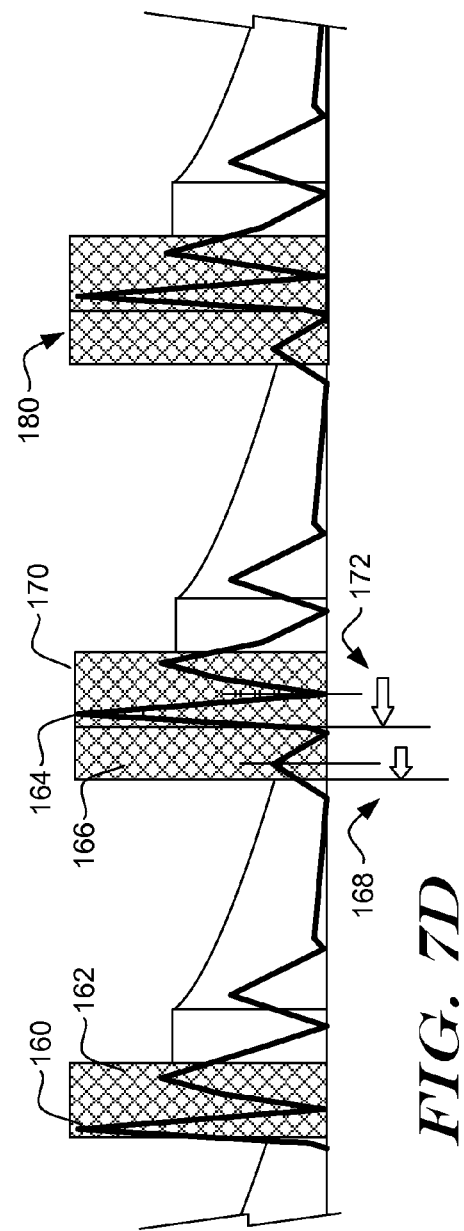

FIGS. 7C-7D compare detection without refractory shifting (FIG. 7C) to detection including refractory shifting (FIG. 7D). In FIG. 7C, a series of QRS complexes are shown beginning with the QRS at 140. A refractory period 142 and detection profile are shown relative to QRS 140.

The P-wave that precedes the next QRS 144 causes a detection that triggers refractory 146. Due to the early detection of QRS 144, the latter portion of the QRS is detected as an overdetection leading to refractory 148 and detection profile. Because of the later detection at 148, the P-wave preceding the next QRS complex 150 is not detected, and instead the R-wave is detected causing refractory 152.

The result is 3:2 overdetection where 2 beats lead to 3 detected events. For overdetection algorithms that check for patterns of overdetection, such as 2:1 overdetection, this 3:2 overdetection may present difficulties.

FIG. 7D illustrates how shifting the refractory period starting point can turn 3:2 overdetection into 2:1 overdetection. By making the overdetection more "regular," this overdetection may improve the function of overdetection identification methods or systems that rely on pattern identification. In the example of FIG. 7D, the first QRS complex at 160 is single detected as shown by the refractory period at 162. The P-wave of the next QRS complex 164 is detected early. The "Seek" Interval here does not identify the R-wave for QRS complex 164 and instead focuses on the P-Wave (similar to FIG. 7A). The result is that the method shifts the start of refractory period 166 to a set time before the P-wave peak at shown at 168, using a rule similar to the example in FIG. 6B.

The trailing portion of the QRS complex 164 is detected as well, causing refractory period 170. The shifting of refractory period 166 causes this latter detection earlier into the QRS complex. In addition, the refractory period 170 is also shifted earlier as shown at 172 to align with the R-wave which, in this instance, falls within the "Seek" Interval, similar to FIG. 7B. In effect, the refractory periods 166, 170 actually overlap, though the detection causing refractory period 170 fell outside of refractory period 166.

The next effect of these manipulations of the refractory period start points for refractory periods 166 and 170 is to cause double detection of the next R-wave at 180. The repeated double detection may be more amenable to pattern-seeking double detection algorithms. For example, intervals between detections will be consistently long-short-long-short in FIG. 7D, rather than long-short-long-long in FIG. 7C. Using a histogram approach as in U.S. Pat. No. 6,505,068 to Bonnett et al. would likely have more success identifying overdetection, for example, when overdetection is repeated throughout the several cardiac cycles. Such consistent overdetection may also enhance methods such as those in U.S. Pat. Nos. 8,160,686 and 8,160,687, each titled METHODS AND DEVICES FOR ACCURATELY CLASSIFYING CARDIAC ACTIVITY, U.S. Pat. No. 8,265,737, titled METHODS AND DEVICES FOR IDENTIFYING OVERDETECTION OF CARDIAC SIGNALS, and/or US Published Patent Application No. 2012-0046563, titled METHODS AND DEVICES THAT IDENTIFY OVERDETECTION IN IMPLANTABLE CARDIAC SYSTEMS.

Figure 8:
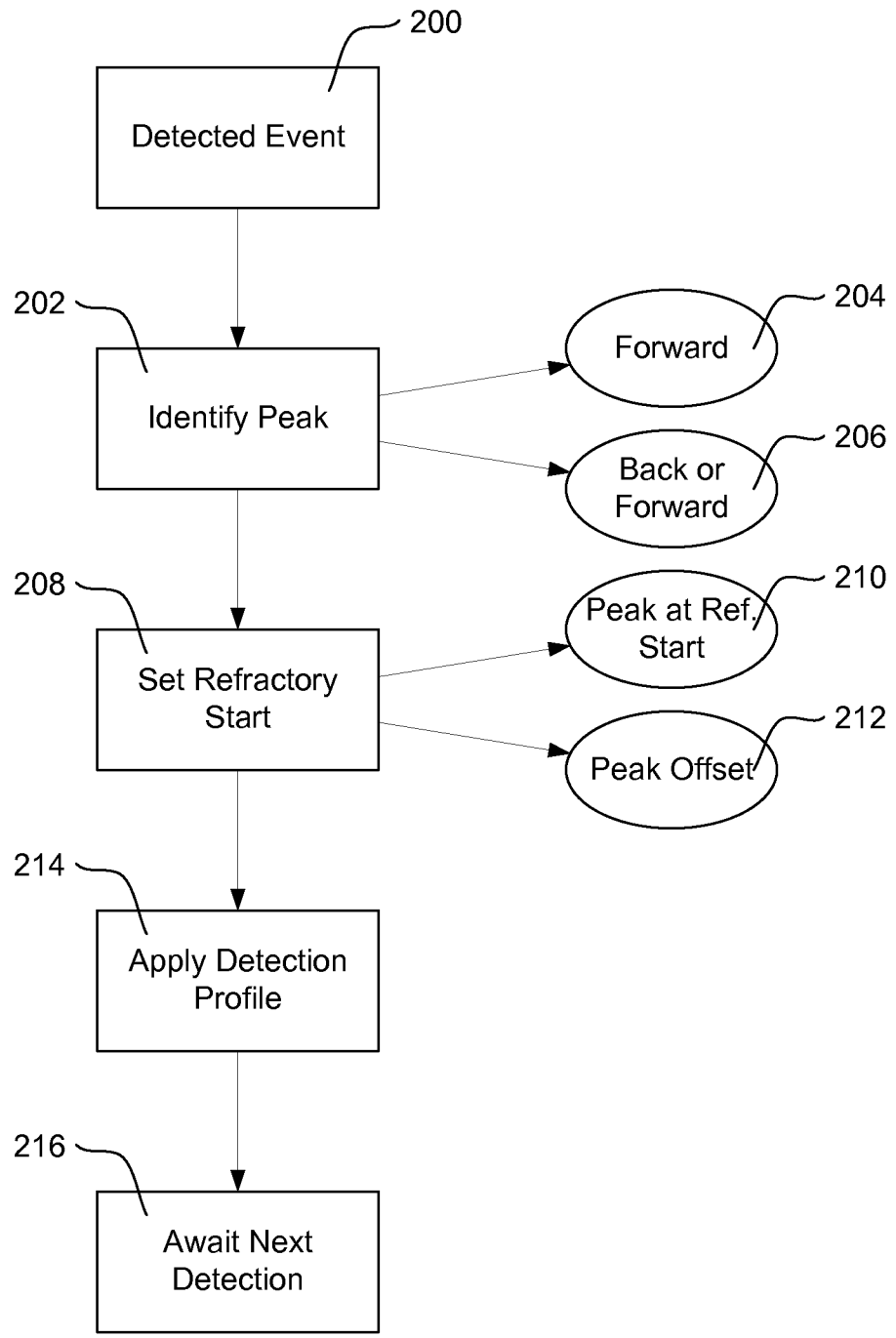
FIG. 8 is a block diagram for an illustrative method.

FIG. 8 is a block diagram for an illustrative method for tailored detection of cardiac cycles. The method is iterative, beginning from a detected event at 200. The detected event 200 may be a detection threshold crossing such as those illustrated variously above in FIGS. 2-5, 6(a-b) and 7(a-d). The detected event 200 may be defined in some other way, such as by a maximum slew location in the signal, by using a peak or threshold for a first or second derivative, using a pattern matching or shape matching formula, or by observing a subset of data or points to observe a detection feature, with such alternative methods having been discussed throughout the art.

The method in FIG. 8 next identifies a relevant peak 202 during a Seek Interval. The Seek Interval may be defined to be "Forward" 204 and include some period of time, for example, fifty to three-hundred milliseconds, after the detected event 200. The Seek Interval may instead be defined to be "Back or Forward" 206 and include some period of time, from up to one-hundred milliseconds before to two hundred milliseconds after the detected event 200.

Once the relevant peak is identified 202, the start of refractory is set 208. In one example, the point in time for the relevant peak that was found at 202 becomes the starting point for the refractory period, as shown at 210. In another example, an offset is defined to start refractory period before or after the point in time for the relevant peak, as shown at 212. Illustrative offsets may be in the range up to 100 milliseconds before or after the relevant peak.

Those skilled in the art will recognize that other ranges may be used. In some examples, rather than having a system determine the start point for refractory to implement these methods, the implementation may be designed to simply define an endpoint for refractory relative to the identified peak. For example, an application may set the end of refractory to 50 to 250 milliseconds after the identified peak. Those skilled in the art will recognize that some such settings will be generally equivalent to one another, for example, in effect, it would be largely the same to set the start of refractory to 100 milliseconds before the identified peak, if refractory is 250 milliseconds long, as it would be to simply define the end of refractory at 150 milliseconds after the peak.

Following the setting of refractory start at 208 (or in an alternative, the refractory end) relative to the identified peak 202, the method then applies the detection profile at 214. The detection profile is applied until the next detection occurs 216, and the method iterates back to block 200. In some examples, such iterations are continuous. In other examples, a rule may be set to perform the method as shown only when detected rates are high, or when intervals between detected events become highly variable, or according to some other rule.

Figure 9:
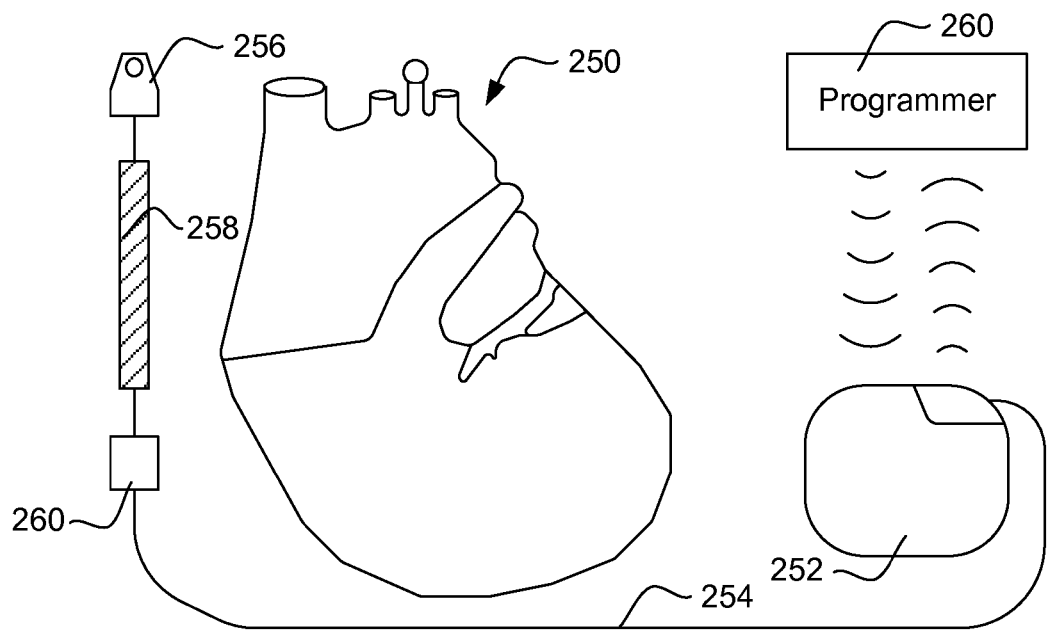
FIGS. 9-10 show implant locations for illustrative cardiac systems.
Figure 10:
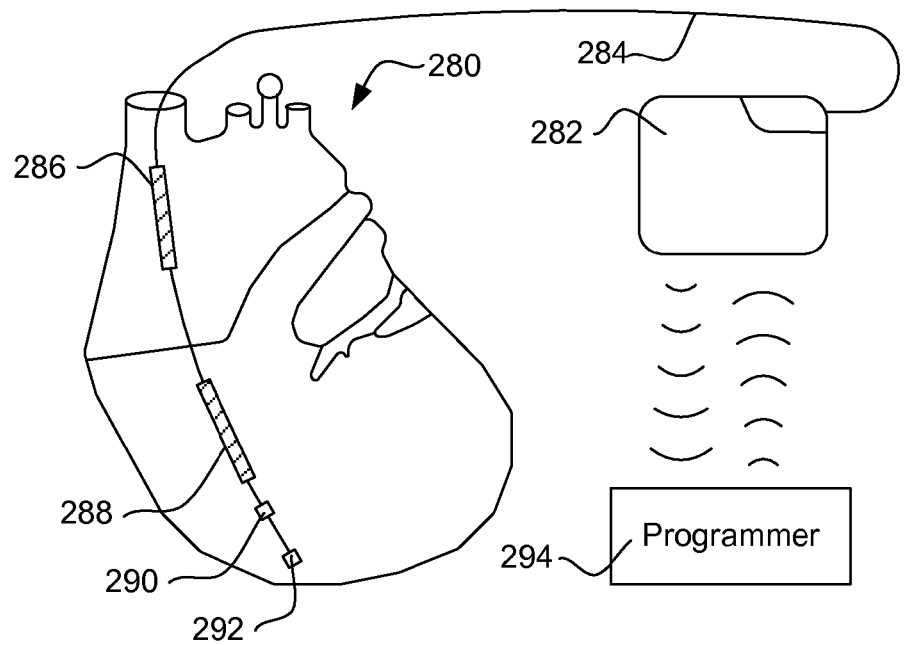

FIGS. 9-10 show implant locations for illustrative cardiac systems. The present invention may find application in a subcutaneous-only system as illustrated in FIG. 9, or in a transvenous system as shown in FIG. 10. Alternatives may include systems having multiple subcutaneous and transvenous elements, epicardial systems, or fully intravenous or intracardiac systems.

The illustrative system shown in FIG. 9 is shown relative to a heart 250 and is intended to convey a subcutaneous implant that would take place over the ribs of the patient and beneath the patient's skin. A canister 252 is implanted near the left axilla, with lateral, anterior, or posterior positions being possible. A lead 254 couples the canister 252 to electrodes 256, 258 and 260, which are illustrated as implanted along the sternum of the patient, typically to the left or right thereof. The system in FIG. 9 may include an external programmer 260 configured for communication with the implant 252.

The system in FIG. 10 is a transvenous system, illustratively shown relative to the heart 280 again with the patient's ribs omitted for clarity. The canister 282 is in a high pectoral position, with the lead 284 accessing the vasculature and entering the heart. The lead 284 may include a superior vena cava coil electrode 286, a right ventricular coil electrode 288, and one or two ventricular sense/pace electrodes 290, 292. Again a programmer is shown at 294 and configured for communication with the implanted system. The system may further include a left ventricular lead (not shown).

Communication for either of the systems in FIG. 9 or 10 may be inductive, RF or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

The canisters in FIGS. 9 and 10 will typically contain operational circuitry for the implantable system. The operational circuitry may include a controller and any suitable analog and/or digital circuits needed for signal processing, memory storage and generation of high-power electrical, low-power electrical and/or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes. The leads and external shell for the canisters can be manufactured with various materials suitable for implantation, such as those widely known, along with coatings for such materials, throughout the art. For example, the canisters can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes can be formed of suitable materials as well, such as silver, gold, titanium or stainless steel such as MP35N stainless steel alloy, or other materials.

The location of system implant may vary. For example, the system shown is a subcutaneous-only system located on the anterior and lateral chest between the skin and ribcage of the patient. Other subcutaneous only systems (including systems without a lead 254, with multiple leads 254, or an array in place of lead 254) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular.

Other systems may include one or more transvenous leads or epicardial leads/electrodes, and may use different canister implant locations, such as placing the canister in a higher pectoral position closer to the clavicle for closer venous access, or abdominal placement. Illustrative transvenous systems include single chamber, dual chamber and biventricular systems. A fully intravenous system has also been proposed. Additional or other coatings or materials than those noted above may be used, particularly for epicardial, transvenous or intravenous systems, leads and canisters.

Various alternatives and details for these designs, materials and implantation approaches are known to those skilled in the art. Commercially available systems in which the above methods can be performed or which may be configured to perform such methods are known including the Boston Scientific Teligen® ICD and S-ICD® System, Medtronic Concerto® and Virtuoso® systems, and St. Jude Medical Promote® RF and Current® RF systems. Such platforms include numerous examples and alternatives for the operational circuitry, battery, canister, lead, and other system elements.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of detecting QRS complexes in an implantable medical device system, the implantable medical device system comprising at least two electrodes for sensing cardiac activity coupled, electrically, to operational circuitry for analyzing sensed cardiac activity, the method comprising the operational circuitry:
applying a time-changing detection threshold to a sensed signal until the sensed signal crosses the detection threshold, wherein the detection threshold includes a first time period during which the operational circuitry will not detect an event, and at least a second time period after the first time period during which the operational circuitry will detect an event upon crossing of the detection threshold by a sensed signal;
declaring a first detected event in association with the sensed signal crossing the detection threshold;
identifying a peak having a highest amplitude during a seeking interval that includes the point in time when the sensed signal crossed the detection threshold leading to the first detected event; and
re-applying the time-changing detection threshold to the sensed signal after the identified peak such that the first time period begins at a time corresponding to the identified peak.

2. The method of claim 1 wherein the time corresponding to the identified peak occurs after the point in time where the sensed signal crossed the detection threshold leading to the first detected event.

3. The method of claim 1 wherein the time corresponding to the identified peak occurs before the point in time where the sensed signal crossed the detection threshold leading to the first detected event.

4. The method of claim 1 wherein the seeking interval includes approximately 100 milliseconds of time before the sensed signal crossing the detection threshold and approximately 200 milliseconds of time after the sensed signal crossing the detection threshold.

5. The method of claim 1 wherein the seeking interval begins at the time that the sensed signal crossed the detection threshold and ends approximately 200 milliseconds later.

6. The method of claim 1 wherein the step of re-applying the time-changing detection threshold such that the first time period begins at a time corresponding to the identified peak is performed such that the first time period begins approximately 50 milliseconds before the identified peak.

7. A method of detecting QRS complexes in an implantable medical device system, the implantable medical device system comprising at least two electrodes for sensing cardiac activity coupled, electrically, to operational circuitry for analyzing sensed cardiac activity, the method comprising the operational circuitry:
applying a time-changing detection threshold to a sensed signal until the sensed signal crosses the detection threshold, wherein the detection threshold includes a first time period during which the operational circuitry will not detect an event, and at least a second time period after the first time period during which the operational circuitry will detect an event upon crossing of the detection threshold by a sensed signal;
declaring a first detected event in association with the sensed signal crossing the detection threshold at a first point in time;
identifying a second point in time relative to the first detected event, wherein the second point in time occurs during an interval associated with the first point in time;
re-applying the time-changing detection threshold to the sensed signal after the second point in time, such that the first time period begins at the second point in time, wherein the second point in time and the first point in time are not simultaneous.

8. The method of claim 7 wherein the first point in time and the second point in time are separated by a duration that is calculated by identifying a peak in the sensed signal during the interval associated with the first point in time and determining how far apart, in time, the peak occurs from the first point in time.

9. The method of claim 8 wherein the method further comprises declaring a double detected signal if the peak occurs before the first point in time.

10. The method of claim 7 wherein:
the operational circuitry is configured to store a template for comparison to the sensed signal;
the method further comprises comparing the template to the sensed signal iteratively to identify an alignment between the template and the sensed signal at which a maximum correlation occurs and generating a shift metric indicative of the alignment of the template and the sensed signal that results in maximum correlation; and
defining the second point in time using the shift metric.

11. The method of claim 7 wherein the operational circuitry is configured to apply a set of limits to the second time to ensure that the second time is no more than about 100 milliseconds before the first time and no more than about 200 milliseconds after the first time.

12. The method of claim 7 wherein the operational circuitry is configured to apply a set of limits to the second time to ensure that the second time is no more than a preset duration away from the first time.

13. The method of claim 7 wherein the operational circuitry is configured to apply a set of limits to the second time to ensure that the second time is no more than a preset duration after the first time.

14. The method of claim 7 wherein the second point in time is defined by the operational circuitry relative to a peak of the sensed signal.

15. An implantable medical device system comprising at least two electrodes for sensing cardiac activity coupled, electrically, to operational circuitry for analyzing sensed cardiac activity, the operational circuitry being configured to identify QRS complexes of a sensed signal captured using the electrodes by the following:
the operational circuitry comparing a time-changing detection threshold to the sensed signal captured from the electrodes, until the sensed signal crosses the detection threshold, wherein the detection threshold includes a first time period during which the operational circuitry will not detect an event, and at least a second time period after the first time period during which the operational circuitry will detect an event upon crossing of the detection threshold by a sensed signal;
the operational circuitry declaring a first detected event in association with the sensed signal crossing the detection threshold at a first point in time;
the operational circuitry identifying a second point in time relative to the first detected event, wherein the second point in time occurs during an interval associated with the first point in time;

the operational circuitry re-applying the time-changing detection threshold to the sensed signal after the second point in time such that the first time period begins at the second point in time, the operational circuitry being configured such that the second point in time and the first point in time are not simultaneous.

16. The implantable medical device system of claim 15 wherein the operational circuitry is configured such that the first point in time and the second point in time are separated by a duration that is calculated by identifying a peak in the sensed signal during an interval associated with first point in time and determining how far apart, in time, the peak occurs from the first point in time.

17. The implantable medical device of claim 16 wherein the operational circuitry is further configured to declare a double detected signal if the peak occurs before the first point in time.

18. The implantable medical device of claim 15 wherein:
the operational circuitry is configured to store a template for comparison to the sensed signal;
the operational circuitry is also configured to compare the template to the sensed signal iteratively to identify an alignment between the template and the sensed signal at which a maximum correlation occurs and generating a shift metric indicative of the alignment of the template and the sensed signal that results in maximum correlation; and the operational circuitry is configured to define the second point in time using the shift metric.

19. The implantable medical device of claim 15 wherein the operational circuitry is configured to apply a set of limits to the second time to ensure that the second time is no more than a preset duration away from the first time.

20. The implantable medical device of claim 15 wherein the operational circuitry is configured to identify a peak in the sensed signal and select the second point in time relative to the peak.

* * * * *